(12) United States Patent
Fitzgerald et al.

(10) Patent No.: US 8,617,828 B2
(45) Date of Patent: Dec. 31, 2013

(54) GLUTATHIONE S-TRANSFERASE OMEGA 1 WILD TYPE SPECIFIC ANTIBODY

(75) Inventors: Peter Stephen Fitzgerald, Antrim (GB); Ivan Robert McConnell, Antrim (GB); Philip Andrew Lowry, Antrim (GB); Elouard Benchikh, Antrim (GB)

(73) Assignee: Randox Laboratories Limited, Antrim (GB)

( * ) Notice: Subject to any disclaimer, the term of this patent is extended or adjusted under 35 U.S.C. 154(b) by 0 days.

(21) Appl. No.: 13/421,517

(22) Filed: Mar. 15, 2012

(65) Prior Publication Data

US 2012/0237947 A1    Sep. 20, 2012

(30) Foreign Application Priority Data

Mar. 15, 2011    (GB) .................................. 1104286.8

(51) Int. Cl.
| | | |
|---|---|---|
| G01N 33/53 | (2006.01) | |
| G01N 33/573 | (2006.01) | |
| C07K 16/40 | (2006.01) | |
| A61K 38/04 | (2006.01) | |
| A61K 38/08 | (2006.01) | |

(52) U.S. Cl.
USPC ............................ 435/7.1; 530/300; 530/328

(58) Field of Classification Search
None
See application file for complete search history.

(56) References Cited

FOREIGN PATENT DOCUMENTS

WO    WO 99/38973    * 8/1999
WO    WO 2006/134390    * 12/2006

OTHER PUBLICATIONS

Roitt et al. (Immunology, 1993, Mosby, St. Louis, p. 6.4-6.5).*
Agusa et al, "Genetic Polymorphisms Influencing Arsenic Metabolism in Human: Evidence from Vietnam", 2008, pp. 179-185, Interdisciplinary Studies on Environmental Chemistry—Biological Responses to Chemical Pollutants.
Chung et al, "Gene polymorphisms of glutathione S-transferase omega 1 and 2, urinary arsenic methylation profile and urothelial carcinoma", 2011, pp. 465-470, vo. 409, Science of the Total Environment.
Marahatta et al, "Polymorphism of glutathione S-transferase Omega gene and risk of cancer", 2006, pp. 276-281, Cancer Letters.
Czlonkowska et al, "Immune processes in the pathogenesis of Parkinson's disease—a potential role for microgila and nitric oxide", Aug. 7, 2002, vol. 8, No. 8, pp. RA165-177, MedSciMonit—Review Article.
Chen et al, "Comparative proteomic analysis of differentially expressed proteins in human pancreatic cancer tissue", Apr. 15, 2009, vol. 8, No. 2, pp. 193-200, Hepatobiliary Pancreat Dis. Int.
Chronopoulou et al, "Glutathione Transferases: Emerging Multidisciplinary Tools in Red and Green Biotechnology", 2009, vol. 3, pp. 211-223, Recent Patents on Biotechnology.
Board et al, "Identification, Characterization, and Crystal Structure of the Omega Class Glutathione Transferases", 2000, vol. 275, No. 32, pp. 24798-24806, The Journal of Biological Chemistry.
Chariyalertsak et al, "Role of glutathione S-transferase omega gene polymorphisms in breast-cancer risk", 2009, vol. 95, pp. 739-743, Tumori.
Tanaka-Kagawa et al, Functional characterization of two variant human GSTO 1-1s (Ala140Asp and Thr217Asn), 2003, vol. 301, pp. 516-520, Biochemical and Biophysical Research Communications.
Strange et al, "Glutathione-S-transferase family of enzymes", 2001, vol. 482, pp. 21-26, Mutation Research.
Liu et al, "Proteomic analysis of Tiam1-mediated metastasis in colorectal cancer", 2007, vol. 31, pp. 805-814, Cell Biology International.
Yin et al, "Immunohistochemistry of Omega Class Glutathione S-Transferase in Human Tissues", 2001, vol. 49, No. 8, pp. 983-987, The Journal of Histochemistry of Cytochemistry.
Griffin et al, "Interleukin-1 in the genesis and progression of and risk for development of neuronal degeneration in Alzheimer's disease", Aug. 2002, vol. 72, pp. 233-238, Journal of Leukocyte Biology.
Harju et al, "Glutathione S-transferase omega in the lung and sputum supernatants of COPD patients", 2007, vol. 8, No. 48, Respiratory Research.
Kolsch et al, "Polymorphisms in glutathione S-transferase omega-1 and AD, vascular dementia, and stroke", Dec. 2004, vol 63, pp. 2255-2260, Neurology.
Pongstaporn et al, "Polymorphism of glutathione S-transferase Omega gene: association with risk of childhood acute lymphoblastic leukemia", 2009, vol. 135, pp. 673-678, J Cancer Res Clin Oncol.
Piaggi et al, "Glutathione transferase omega 1-1 (GSTO1-1) plays an anti-apoptotic role in cell resistance to cisplatin toxicity", 2010, vol. 31, No. 5, pp. 804-811, Carcinogenesis.
Li et al, "Glutathione S-transferase omega-1 modifies age-at-oneset of Alzheimer disease and Parkinson disease", 2003, vol. 12, No. 24, pp. 3259-3267, Human Molecular Genetics.
Purisa et al, "Association Between GSTO1 Polymorphism and Clinicopathological Features of Patients with Breast Cancer", pp. 184-189, Thai Cancer Journal.
Wahner et al, "Glutathione S-transferase mu, omega, pi, and theta class variants and smoking in Parkinson's disease", Feb. 21, 2007, vol. 413, No. 3, pp. 274-278, Neurosci. Lett.

* cited by examiner

*Primary Examiner* — Jacob Cheu
*Assistant Examiner* — Carmencita M Belei
(74) *Attorney, Agent, or Firm* — B. Aaron Schulman, Esq.; Stites & Harbison, PLLC.

(57) ABSTRACT

The invention relates to a novel antibody which binds to wild type (wt) Glutathione S-transferase Omega 1 (wtGSTO1) but not to mutant (mut) GSTO1 and methods and uses based on the antibody. The antibody is based on novel haptens and immunogens.

15 Claims, 3 Drawing Sheets wtGSTO1

Figure 1:
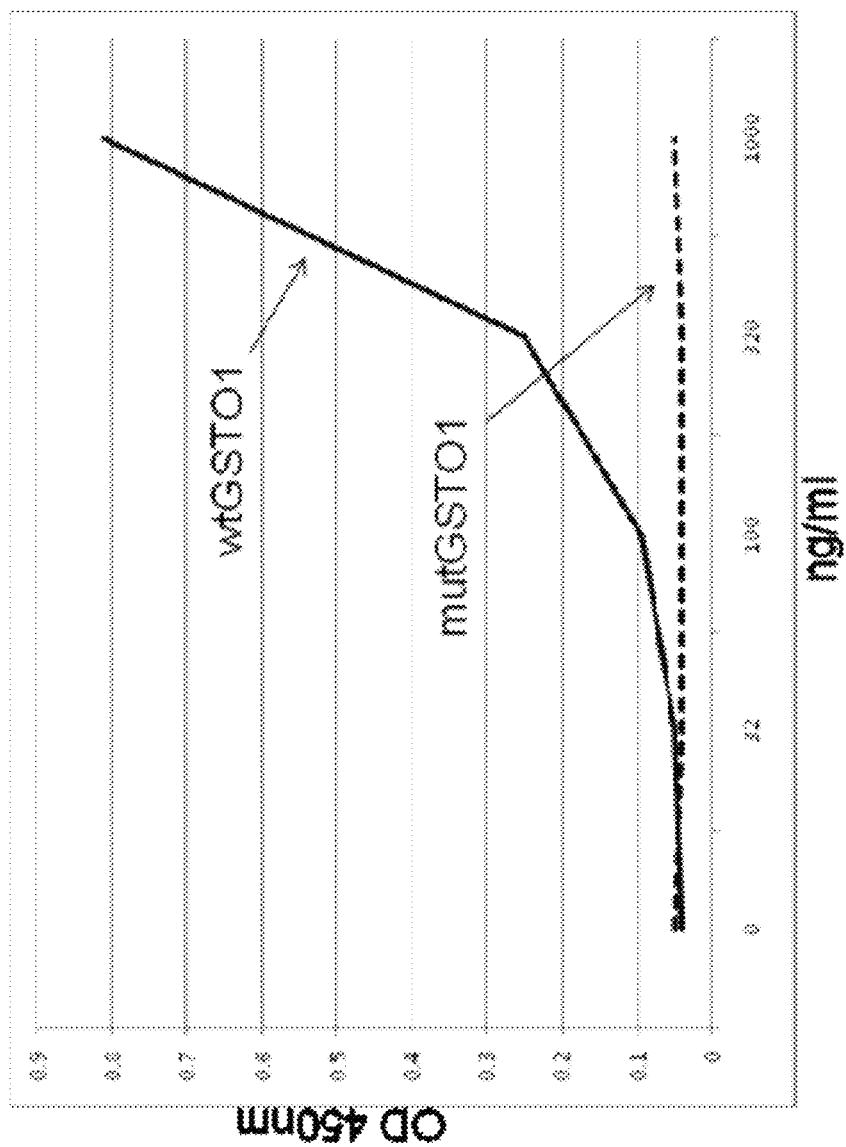

MSGESARSLGKGSAPPGPVPEGSIRIYSMRFCPFAERTRLVLKAKGIRHEVININLKNKPEWFFKKNPFGLVPVLENSQQLIYESAITCE
YLDEAYPGKKLLPDDPYEKACQKMILELFSKVPSLVGSFIRSQNKEEFRKEFTKLEEVLTNKKTFFGGNSISMIDYLIWPW
FERLEAMKLNECVDHTPKLKLWMAAMKEDPTVSALLTSEKDWQGFLELYLQNSPEACDYGL mutGSTO1

MSGESARSLGKGSAPPGPVPEGSIRIYSMRFCPFAERTRLVLKAKGIRHEVININLKNKPEWFFKKNPFGLVPVLENSQQLIYESAITCE
YLDEAYPGKKLLPDDPYEKACQKMILELFSKVPSLVGSFIRSQNKEIDYDGLKEEFRKEFTKLEEVLTNKKTFFGGNSISMIDYLIWPW
FERLEAMKLNECVDHTPKLKLWMAAMKEDPTVSALLTSEKDWQGFLELYLQNSPEACDYGL

Figure 3

GLUTATHIONE S-TRANSFERASE OMEGA 1 WILD TYPE SPECIFIC ANTIBODY

FIELD OF THE INVENTION

The present invention relates to the detection of wtGSTO1 and mutGSTO1 enzymes. Specifically, the invention describes novel immunogens, novel antibodies and methods for detecting wtGSTO1 and mutGSTO1 enzymes, and their use in disease research, diagnosis and treatment.

BACKGROUND

Glutathione transferases (GSTs) are a multi-gene enzyme family which through catalyzing a number of distinct glutathione dependent reactions play critical roles in providing protection against electrophiles and products of oxidative stress. Multiple cytosolic and membrane-bound GST isoenzymes with divergent catalytic and non-catalytic binding properties are found in all eukaryotic species. The mammalian cytosolic GSTs are made up of Alpha (A), Mu (M), Omega (O), Pi (P), Sigma (S), Theta (T) and Zeta (Z) families (Strange et al., 2001). The most recently discovered class of cytosolic GSTs, the Omega class (GSTO1 and GSTO2), are characterised by a unique N-terminal extension and a cysteine residue in the active site, which is distinct from the tyrosine and serine residues associated with other GST classes. GSTO1 (Board et al., 2000) exhibits glutathione-dependent thiol transferase and dehydroascorbate reductase activites characteristic of glutaredoxins and which are not associated with other GSTs. The polypeptide consists of 241 amino acids with a predicted MW of 27.5 kDa but migrates at approximately 56 kDa suggesting it forms dimers under native conditions (Board et al., 2000). The structure of recombinant GSTO1 has been solved at 2 Angstrom resolution (NCBI Protein Database: 1EEM; Board et al., 2000). Expression of GSTO1 is abundant in a wide range of normal tissues including liver, macrophages, glial cells and endocrine cells, as well as myoepithelial cells of the breasts, neuroendocrine cells of the colon, fetal myocytes, hepatocytes, biliary epithelium, ductal epithelium of the pancreas, Hofbauer cells of the placenta and follicular and C-cells of the thyroid (Yin et al., 2001). This widespread expression and conserved sequence suggests that GSTO1 may have a significant house-keeping role and biological functions distinct from other GSTs.

The literature contains numerous reports on the role of GSTs in various stages of disease progression and treatment. Whereas the role of GSTs is largely beneficial in deactivating and detoxifying potentially dangerous chemicals, it appears that sometimes they have a detrimental effect in the body. For instance, over-expression has been linked with various forms of cancer, for example GSTO1 may be up-regulated in both colorectal (Liu et al., 2007) and pancreatic cancer (Chen et al., 2009). Over-expression of GSTO1 is also correlated with the onset of drug resistance of cancer cells. This may be the result of an association with the activation of survival pathways (Akt and ERK1/2) and inhibition of apoptotic pathways such as JNK1 and protection against cisplatin induced apoptosis (Piaggi et al., 2010).

Genetic variation in GSTs has been reported to represent a risk factor for a variety of diseases including many forms of cancer. A single nucleotide polymorphism (SNP) at base 419 (419C>A) of GSTO1 results in an alanine to aspartate substitution in amino acid 140 (A140D). Tanaka-Kagawa et al., (2003) functionally characterised recombinant GSTO1 Ala140Asp variants and discovered that enzyme activity decreased from that of WT (Ala/Ala) for particular substrates. This change in activity is a likely contributor to this SNPs role in disease. Polymorphisms in GSTO1 affecting the enzymes ability to metabolise inorganic arsenic have also been found (Chung et al., 2011; Agusa et al., 2008), leading to differences in individuals susceptibility to arsenic toxicity. The GSTO1 A140D polymorphism could play an important role as a risk factor for the development of heptacellular carcinoma, cholangiocarcinoma and breast cancer (Marahatta et al., 2006). The presence of WT (Ala/Ala) is more likely amongst cases of advanced stage breast cancer (Purisa et al., 2008; Chariyalertsak et al., 2009). The GSTO1 A140D polymorphism has also been associated with the risk of acute lymphoblastic leukaemia (ALL) in children and may also be involved in development of the disease (Pongstaporn et al., 2009). A role in chronic obtrusive pulmonary disease (COPD) has also been proposed (Harju et al., 2007).

Studies also suggest that GSTO1 is a risk indicator for Alzheimer's disease (AD) and Parkinson's disease (PD). Li et al., (2003) reported a difference in the gene expression of GSTO1 between AD patients and controls and that the single polymorphism rs4925 (equivalent to the Ala140Asp mutation) was linked to later age-at-onset (AAO) of both AD and PD. Kolsch et al., (2004) also found that GSTO1 polymorphisms were associated with an earlier AAO and increased the risk of vascular dementia and stroke. Although these contrasting findings could suggest that the SNP is not the causal factor in AAO, an association is present and warrants further investigation into its use as a marker. A recent study also supports a role for the GSTO1 Ala140Asp SNP in sporadic AD (Capurso et al., 2010) which is the most common form of AD. Wahner et al., (2007) found a 32% risk reduction for PD among subjects carrying one or more GSTO1 variant allele compared to the wild type.

Circumstantial evidence further supporting GSTO1 as having a role in neurodegenerative disorders includes cellular co-localization with IL-1β, which is over-expressed in the brains of both AD and PD patients (Griffin & Mrak, 2002; Czlonkowska et al., 2002) and is a fundamental component of the inflammatory response that is proposed to contribute to the pathogenesis of both AD and PD. Chronopoulou & Labrou (2009) have hypothesised that it is the dehydroascorbate reductase role of GSTO enzymes in the brain which is the basis of their genetic link to AAO in AD and PD.

It is evident from the primary literature that further research as to the role of WT and mut GSTO1 in disease is desirable and an analytical method which facilitates this is required. Single nucleotide polymorphisms (SNPs) are the most abundant form of genetic variation in humans and are associated with differences in disease risk, susceptibility, progression and success of treatment. Genotyping of SNPs is important in disease diagnosis and prognosis and is a key driving force in the expanding sector of personalized medicine. Genotyping techniques which are underpinned by the polymerase chain reaction (PCR) are costly and time-consuming and only enable a 'risk analysis' approach to disease diagnostics. In vitro protein detection includes techniques based on electrophoresis, mass spectrometry and antibodies, but each has potential weaknesses with respect to the current problem of wtGSTO1 and mutGSTO1 protein discrimination, in which the structural difference is a single amino acid (out of the 241 of the full protein). For example, electrophoresis is likely to be insufficiently sensitive, mass spectrometry is unlikely to produce distinctive fragmentation patterns, and antibodies to either wild type or mutant are likely to cross-react.

The inventors describe herein an antibody with surprising specificity for wtGSTO1.

References

Agusa, T. et al., (2008). Genetic Polymorphisms Influencing Arsenic Metabolism in Human: Evidence from Vietnam. *Interdisciplinary Studies on Environmental Chemistry—Biological Responses to Chemical Pollutants*, Eds., Murakami, Y., Nakayama, K., Kitamura, S.-I., Iwata, H., and Tanabe, S. pp. 179-185.© by TERRAPUB, 2008.

Board, P. G. et al., (2000). Identification, Characterization, and Crystal Structure of the Omega Class Glutathione Transferases. *The Journal of Biological Chemistry,* 275, 24798-24806.

Capurso, C. et al., (2010). Polymorphisms in Glutathione S-Transferase Omega-1 Gene and Increased Risk of Sporadic Alzheimer Disease. *Rejuvenation Research*-Not available-, ahead of print. doi:10.1089/rej.2010.1052.

Chariyalertsak, S. et al., (2009). Role of glutathione S-transferase omega gene polymorphisms in breast-cancer risk. Tumori, 95: 739-743.

Chen, J-H. et al., (2009). Comparative proteomic analysis of differentially expressed proteins in human pancreatic cancer tissue. *Hepatobiliary & Pancreatic Diseases International,* 8, 193-200.

Chronopoulou, E. G. and Labrou, N. E. (2009). Glutathione Transferases: Emerging Multidisciplinary Tools in Red and Green Biotechnology. *Recent Patents on Biotechnology,* 3 (3), 211-223(13).

Chung, C-J. et al., (2011). Gene polymorphisms of glutathione S-transferase omega 1 and 2, urinary arsenic methylation profile and urothelial carcinoma. *Science of The Total Environment,* 409 (3), 465-470.

Czlonkowska, A. et al., (2002) Immune processes in the pathogenesis of Parkinson's disease—a potential role for microglia and nitric oxide. *Medical Science Monitor.,* 8, RA165-RA177.

Griffin, W. S, and Mrak, R. E. (2002) Interleukin-1 in the genesis and progression of and risk for development of neuronal degeneration in Alzheimer's disease. *Journal of Leukocyte. Biology.,* 72, 233-238.

Harju, T. H. et al., (2007). Glutathione S-transferase omega in the lung and sputum supernatants of COPD patients. *Respiratory Research,* 8 (48).

Kölsch, H. et al., (2004). Polymorphisms in glutathione s-transferase omega-1 and AD, vascular dementia, and stroke. *Neurology,* 63, 2255-2260.

Li, Y-J. et al., (2003). Glutathione S-transferase omega-1 modifies age-at-onset of Alzheimer disease and Parkinson disease. *Human Molecular Genetics,* 12 (24), 3259-3267.

Liu, L et al., (2007). Proteomic analysis of Tiam1-mediated metastasis in colorectal cancer. *Cell Biology International,* 31 (8), 805-814.

Marahatta, S. B. et al., (2006). Polymorphism of glutathione S-transferase Omega gene and risk of cancer. *Cancer Letters,* 236 (2), 276-281.

Piaggi, S., et al., (2010). Glutathione transferase omega 1-1 (GSTO1-1) plays an anti-apoptotic role in cell resistance to cisplatin toxicity. *Carcinogenesis,* 31 (5): 804-811.

Pongstaporn, W. et al., (2009). Polymorphism of glutathione S-transferase Omega gene: association with risk of childhood acute lymphoblastic leukemia. *Journal of Cancer Research and Clinical Oncology,* 135 (5), 673-678.

Purisa, W. et al., (2008). Association between GSTO1 Polymorphism and Clinicopathological Features of Patients with breast cancer. *Thai Cancer Journal,* 28 (4) 185-189.

Strange, R. C. et al., (2001). Glutathione-S-transferase family of enzymes. *Mutation Research/Fundamental and Molecular Mechanisms of Mutagenesis,* 482 (1-2), 21-26.

Tanaka-Kagawa, T. et al., (2003). Functional characterization of two variant human GSTO1-1s (Ala140Asp and Thr217Asn). *Biochemical and Biophysical Research Communications,* 301 (2), 516-520.

Wahner, A. D. et al., (2007). Glutathione S-transferase mu, omega, pi, and theta class variants and smoking in Parkinson's disease. *Neuroscience Letters,* 21; 413(3): 274-278.

Yin, Z-L. et al., (2001) Immunohistochemistry of Omega Class Glutathione S-Transferase in Human Tissues. *Journal of Histochemistry & Cytochemistry,* 49 (8), 983-987.

US Patent Application—US2008/0318229—*Method for diagnosing Neuro-degenerative Disease*

SUMMARY OF THE INVENTION

The invention describes a novel monoclonal antibody specific to wtGSTO1 which enables immunoassay methods for the detection and determination of wtGSTO1 and mutGSTO1. The immunoassays have application, for example, in disease research. The invention is underpinned by a novel immunogen which enables the production of said antibodies.

DRAWINGS

FIG. 1 A cross-reactivity study for the cell line GST1.1H7.D2.E2.D7.D5.G2.F2. A supernatant assay was used; ELISA plates were coated with recombinants and detected via anti-species HRP. <0.1% cross-reactivity with mutGSTO1 was found.

Figure 2:
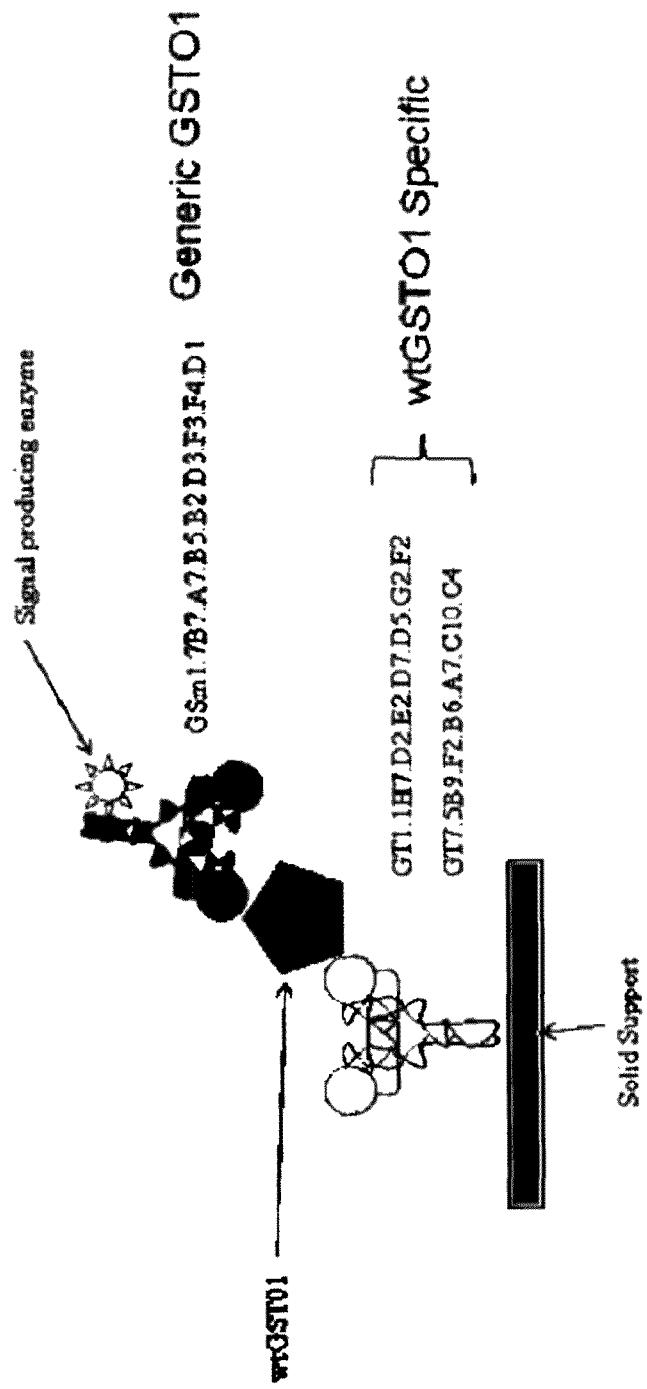

FIG. 2 wtGSTO1 Sandwich assay.

FIG. 3 Amino acid sequences of wtGSTO1 (SEQ ID NO 3) and mutGSTO1 (SEQ ID NO 4). Peptides used in immunogen preparations are highlighted.

DETAILED DESCRIPTION OF THE INVENTION

Unless otherwise stated technical terms are used according to the conventional usage as known to those skilled in the art.

The first aspect of the invention relates to a polypeptide hapten comprising the structure:

```
Lys-Glu-Asp-Tyr-Ala-Gly-Leu-Lys    (SEQ ID NO 1)
``` attached to a cross-linking group.

Most preferably the polypeptide hapten is of the structure:

```
                                    (SEQ ID NO 2)
        Cys-Lys-Glu-Asp-Tyr-Ala-Gly-Leu-Lys
``` wherein the cross-linking group is attached to the sulphur atom of Cys.

The term "hapten" as used herein describes a pre-immunogenic molecule that stimulates antibody production only when conjugated to a larger carrier molecule. The terms "peptide" and "polypeptide", can be used interchangeably and designate a chain of amino acid based polyamides. The chain can vary in length anywhere from 2 amino acids to 100 or more amino acids. Preferably the peptide is 5-12 amino acids in length and spans the region containing the 140$^{th}$ amino acid in the peptide sequence for the full native GSTO1 protein. Most preferably the polypeptide is 9 amino acids in length and incorporates a terminal cysteine residue. The sulphur atom of the cysteine residue can be conjugated to a large carrier molecule via a crosslinking agent, to form an immunogen. It will, however, be appreciated that the haptens of the invention may be conjugated to a large carrier molecule, optionally via a crosslinking agent, via other residues. For example, one of the Lys residues (either C or N terminal), the Asp residue, or the Glu residue may be used to conjugate to a large carrier molecule, optionally via a crosslinking group. Preferably, conjugation via the Cys residue is preferred.

The term "A140D" refers to the substitution at the $140^{th}$ amino acid position on the wild type GSTO1 protein sequence (NP_004823), caused by the single nucleotide polymorphism at base 419 (419C>A; NG_023362) in GSTO1 wherein the wild type condition (wt) has alanine (A) at this amino acid position while the mutant (mut) has aspartic acid (D). An individual can be homozygous Ala/Ala or Asp/Asp or heterozygous Ala/Asp.

A second aspect of the current invention relates to an immunogen used in the preparation of said antibody which consists of a carrier molecule coupled to the polypeptide amino acid sequences described above. The term "immunogen" as used herein, describes an entity that induces an immune response such as production of antibodies or a T-cell response in a host animal The term "carrier molecule" refers to a molecule to which a hapten or antigen can be bound to impart immunogenic properties to the hapten or antigen. The term "carrier molecule" may be used interchangeably with the terms "carrier", "immunogenicity conferring carrier molecule" and "antigenicity conferring carrier material". Suitable carriers include proteins such as bovine serum albumin, bovine thyroglobulin (BTG), ovalbumin, hemocyanin and thyroglobulin molecules as well as liposomes, synthetic or natural polymers and synthetically designed organic molecules. BTG is a preferred carrier. Crosslinking of peptides to proteins to form an immunogen is well known in the art; the term "crosslinker" as used herein is any bifunctional molecule able to covalently join the peptide of the invention to an immunogenicity conferring carrier molecule. A suitable crosslinker is maleimide, or a maleimide derivative, for example when BTG-maleimide is used to form a hapten-carrier (BTG) conjugate via the cysteine residue. In this case, the peptide is coupled to a BTG maleimide carrier through the addition of a non-native cysteine. Although maleimides are the preferred cross-linking group, coupling with the sulfhydryl group of cysteine, other cross-linking groups which could couple this group on the cysteine include haloacetyls and pyridyldisulfides. As discussed above, the Lys residues (either C or N terminal), the Asp residue, or the Glu residue may alternatively be used to conjugate to a large carrier molecule, optionally via a crosslinking group, to form an immunogen. For example, a primary amine group on the side chain of lysine (Lys) could be coupled using a cross-linker selected from N-hydroxysuccinimide esters, imidoesters, PFP esters or hydroxymethyl phosphine. As another example, a carboxyl group on the side chain of aspartic acid (Asp) or glutamic acid (Glu) could be coupled using a carbodiimide cross-linker, EDC or DCC. However, in one preferred embodiment, the conjugation, preferably using a BTG-maleimide, occurs via the cysteine (Cys) residue, as it is desirable to attach the cross-linker to one end of the peptide so that the full sequence is exposed for recognition by the immune system.

A third aspect of the present invention describes an antibody which specifically binds to wild type (wt) GSTO1. The term "antibody" refers to an immunoglobulin or immunoglobulin-like molecule, in a preferred embodiment of the current invention the antibody is a monoclonal antibody but the skilled person will understand that any type of immunoglobulin molecule or fragment thereof can be used, for example polyclonal antibodies, Fab fragments, scFv fragments and any other antigen binding fragments all of which fall within the scope of the current invention. Monoclonal antibodies may be produced by methods known to those skilled in the art, such as but not limited to the method described herein. Any suitable host animal may be used for example, but not limited to sheep, rabbit, mouse, guinea pig or horse. The preferred animal used for immunisation in the current invention is a sheep. Freund's complete adjuvant was used as an immunopotentiator in the primary immunizations while Freund's incomplete adjuvant was used in all subsequent boosts. Those skilled in the art will know that any suitable immunopotentiator can be used in the initial immunization and any further boosts.

A further aspect of the invention is a kit comprising the antibody (or antibodies) of the invention.

Another aspect of the current invention relates to a method of detecting and/or determining or recovering wtGSTO1 in a sample. The term "detecting" refers to qualitatively analysing for the presence or absence of a substance, while "determining" refers to quantitatively analysing for the amount of a substance present. The term "recover" refers to detecting and/or separating wtGSTO1 from a sample. The sample can be any biological fluid or sample in which GSTO1 is found or expected. The method is preferably an ELISA but any suitable immunoassay method may be used for example a radioimmunoassay, magnetic immunoassay or a lateral flow test. The anti-wtGSTO1 can be attached to a solid support for example a biochip. The wtGSTO1 specific antibodies may be used in the assay on their own or with a secondary generic GSTO1 detection antibody i.e. an antibody which binds both wt and mut GSTO1. An example of the ELISA method comprises wtGSTO1 antibody as the capture antibody and a labelled secondary generic GSTO1 antibody as the detector. The label of the labelled conjugate is a detectable label such as an enzyme, a luminescent substance, a radioactive substance or a mixture thereof. The preferred label is horseradish peroxidase. The detector antibody conjugated to the detectable label described above is an example of a detecting agent for use in the methods of the invention, but any suitable detecting agent can be used. The antibodies of the invention recognise a specific epitope of wtGSTO1; another example of a suitable detecting agent is a monoclonal antibody attached to a detectable label the monoclonal antibody being specific to a different epitope of wtGSTO1. The wtGSTO1 antibody of the invention can be combined with one or more other antibodies that detect different analytes as part of a multi-analyte immunoassay.

The wtGSTO1 antibody of the current invention can also be used in sample purification methods; for example it may be attached to an immunoaffinity column and used to remove wtGSTO1 from a sample leaving only mutGSTO1. This can be detected and/or determined in a subsequent immunoassay using a polyclonal or monoclonal antibody.

The invention also describes the use of the antibody of the invention in determining an individual's GSTO1 expression level as an indicator of susceptibility to, diagnosis of, and/or progression of a disease state. The disease state can be any in which GSTO1 has been implicated as a risk indicator or factor including neurodegenerative diseases, such as AD and PD, cerebrovascular diseases, chronic obstructive pulmonary disease and cancer, including hepatocellular carcinoma, cholangiocarcinoma, colorectal cancer, pancreatic cancer, breast cancer and leukaemia. The antibodies described in the invention can also be used in evaluating an individual's resistance to a therapeutic drug.

Another aspect of the current invention relates to the use of the antibody of the invention in determining wtGSTO1 levels in a sample from a person suspected of having a disease condition, in which the wtGSTO1 concentration differs in the disease state when compared to a control or normal range of expression. The sample may be any biological sample including gel filtrated platelets, whole blood, plasma, serum, urine or saliva.

Thus, the invention also relates to methods utilising the antibody for (a) evaluating an individual's susceptibility to disease; (b) disease diagnosis and prognosis; (c) evaluating an individual's resistance to a therapeutic drug; and/or (d) in vitro sample purification.

GENERAL METHODS, EXAMPLES AND RESULTS

Production of Human Recombinant (hr) GSTO1 Proteins

The following proteins were created at Randox Laboratories, hrGSTO1 140A Wild Type (wtGSTO1) comprising a 241 amino acid fragment (1-241) corresponding to the GSTO1 wild type mature protein (FIG. 3, SEQ ID NO 3) and hrGSTO1 140D mut (mutGSTO1) comprising a 241 amino acid fragment (1-241) corresponding to the GSTO1 mutant mature protein (FIG. 3, SEQ ID NO 4). Each protein was expressed in *E. coli* with an amino-terminal hexahistidine tag.

Peptide Synthesis

The peptides used in the preparation of both wild type and mutant GSTO1 immunogens were synthesised using standard techniques by Bachem Ltd (UK). Such techniques are described, for example, in Barany et al (1987) International Journal of Peptide and Protein Research, Vol 30, Issue 6, pp 705-739.

Conjugation of WTGSTO1 peptide (C-K-E-D-Y-A-G-L-K) (SEQ ID NO 2) to BTG-Maleimide The WTGSTO 1 peptide (7.5 μmol) was dissolved in phosphate buffer (20 mM NaP, 0.15M NaCl, pH 7.5), to this solution was added TCEP (1 eq) in 0.5 ml of the same buffer and the mixture was incubated for 2 hrs at room temperature. This solution was added to a solution of BTG-maleimide (100 mg) in 10 ml of PBS (0.1M NaP, 0.15M NaCl and 1 mM EDTA, pH 7.0) and the mixture was incubated for 4 hrs at RT and overnight at 4° C. The mixture was dialysed against 4 L of PBS pH 7.2, 3 times over a period of 24 hours, and freeze-dried.

Conjugation of mutGSTO1 peptide (C-K-E-D-Y-D-G-L-K) (SEQ ID NO: 5) to BTG-Maleimide The mutGSTO 1 peptide (7.5 μmol) was dissolved in phosphate buffer (20 mM NaP, 0.15M NaCl, pH 7.5) to this solution was added TCEP (1 eq) in 0.5 ml of the same buffer and the mixture was incubated for 2 hrs at room temperature. This solution was added to a solution of BTG-maleimide (100 mg) in 10 ml of PBS (0.1M NaP, 0.15M NaCl and 1 mM EDTA, pH 7.0) and the mixture was incubated for 4 hrs at RT and overnight at 4° C. The mixture was dialysed against 4 L of PBS pH 7.2, 3 times over a period of 24 hours, and freeze-dried.

Example 1

Development of Monoclonal Antibodies Specific to WTGSTO1

Pre-immunization blood samples were collected from 16-month-old female Suffolk sheep. On Day 0, each sheep was immunized subcutaneously with 0.1 mg of immunogen, comprising a motif that housed the single amino acid difference between WTGSTO1 and mutGSTO1 conjugated to Bovine thyroglobulin (BTG) (0.25 ml/site over 4 sites). Subsequent boosts, comprising 0.05 mg of the aforementioned immunogen, were administered subcutaneously to each sheep on a monthly basis. Freund's complete adjuvant was used for primary immunizations and Freund's incomplete adjuvant was used for all subsequent injections. Routine bleeds were taken between boosts to monitor the antibody titre, using WTGSTO1 at 1 μg/ml in a direct binding ELISA using polyclonal serum at various dilutions, detected by HRP-conjugated donkey anti-sheep. When the antisera generated by a particular sheep met the required performance criteria, two final peri-nodal boosts were administered, 28 days apart. Four days following the final peri-nodal boost, lymph nodes were harvested from the Left Axillary, Right Axillary, Left Prescapular and Right Prescapular regions. The lymph nodes were first perfused with media and then dissected using scissors and forceps to gently tease apart each piece of lymph node. The scissors and forceps were then used to scrape the remaining lymphocytes from the tissue into the cell suspension. All cells, except those required for the lymph node cell assay (LNCA), were frozen in 90% FBS 10% DMSO at a density of $2\times10^8$. In order to set up the LNCA, lymphocytes from each node location were incubated in a 24 well plate at $1\times10^6$ cells per well at 5% $CO_2$, 37° C. for 7 days. Supernatant was collected from each well for testing as above (polyclonal bleed assessment). The cells from these LNCA plates were then discarded.

The LNCAs were used to determine whether nodes met standard fusion criteria. Fusion of lymphocytes with a heteromyleoma cell-line was carried out at a ratio of approximately 2:1 by adding 0.5 ml Polyethylene glycol 1500 (PEG) slowly, over 1 minute. PEG was then diluted using serum-free DMEM and the two cell types were allowed to stand for 5 minutes before being plated using 140 ml of 20% DMEM P/S, with ×1 hypoxanthine-aminopterin-thymidine (HAT) into 7×96 well plates (200 μl per well). On Day 7, media was replenished on each fusion plate with 20% DMEM P/S, with ×1 HAT and on Day 14, 180 μl/well of supernatant was removed and used to screen Hybridoma culture supernatants by ELISA. The wells were replenished this time with 20% DMEM P/S with ×1 hypoxanthine-thymidine (HT). The hybridoma culture supernatants were initially screened using the method above (polyclonal bleed assessment). In the follow-up screenings mutGST was used to negatively select hybridoma.

Positive hybridomas were cloned to produce stable monoclonal hybridomas using 1% methylcellulose at 37° C., 5% $CO_2$; chosen either from positive fusion wells or from established, but unstable cell lines. Three cell lines GT1.1H7.D2, GT7.5B9.B2 and GT7.5B9.F2 were identified as meeting specifications and were cloned in triplicate (with good supporting assay results (FIG. 1)), before being cloned by limit dilution. Thus, the distinction between the antibodies was achieved by ELISA cross-reactivity studies carried out on cell lines as illustrated in FIG. 1, which showed the wt specificity of the antibodies.

Positive cell lines were confirmed as being monoclonal using limit dilution. Single colonies were identified after 7 days and screened for antibody production. Once confirmed as being stable and 100% clonal, the resulting cell-lines were expanded at 37° C., 5% $CO_2$ for 4 weeks. After 4 weeks, the supernatants were pooled and purified via Protein A purification.

Example 2

Antibody Characterisation

The antibodies were then conjugated to HRP and characterised to isolate sandwich pairs (FIG. 2) using an existing generic GSTO1 antibody (clone GSm1.7B7.A7.B5.B2.D3.F3.F4.D1 that recognizes a common epitope in WT and mut (available from Randox laboratories CAT no. MAB10069)) on the proprietary protein biochip system Evidence© Investigator (Randox patents EP0994355, EP0988893, EP0874242 and EP1273349). These sandwich pairs were then assessed by testing their ability to bind to native WTGSTO1 protein isolated from gel-filtrated platelets (GFP), prepared by sample lysis in 1×RIPA lysis buffer for 1 hr on ice followed by centrifugation of the samples for 3 min at 13.2 K rpm (16.4 K g). The GFPs were obtained from young healthy controls (J72-J76) and therefore AD patients or AD suspects were not used. Samples J74 and J75 were both found to have the highest WTGSTO1 levels using the WTGSTO1 specific antibodies GT1.1H7.D2.E2.D7.D5.G2.F2 and GT7.5B9.F2.B6.A7.C10.C4 (Table 1). These samples were externally confirmed as being A140A genotypes, (Surgical Research Laboratories, Medical University of Vienna) demonstrating the ability of the WTGSTO1 antibodies in determining the amount and genotype of native GSTO1 in patient samples.

TABLE 1

Results from sandwich assays run for patient samples using either wtGST01 specific GT1.1H7.D2.E2.D7.D5.G2.F2 or GT7.5B9.F2.B6.A7.C10.C4 as capture antibody and GSTO1 specific GSm1.7B7.A7.B5.B2.D3.F3.F4.D1 as the detection antibody.

| Sample | MAb—GT1.1H7.D2.E2.D7.D5.G2.F2 | | MAb—GT7.5B9.F2.B6.A7.C10.C4 | |
|---|---|---|---|---|
| | Signal (RLU) | Conc. (ng/ml) | Signal (RLU) | Conc. (ng/ml) |
| J72 | 1918 | 117.96 | 2403 | 117.41 |
| J73 | 3015 | 184.04 | 3208 | 153.13 |
| J74 | 8957 | 529.50 | 10017 | 456.48 |
| J75 | 6710 | 400.54 | 7599 | 346.52 |
| J76 | 1776 | 109.30 | 1952 | 97.10 |

MAb conc. = 0.08 mg/ml

<110> Randox Laboratories Ltd
<120> Glutathione S-Transferase Omega 1 Wild Type Specific Antibody
<130> P104168US00
<150> GB 1104286.8
<151> 2011-03-15
<160> 4
<170> PatentIn version 3.5
<210> 1
<211> 8
<212> PRT
<213> Unknown
<220>
<223> synthetic peptide
<400> 1
Lys Glu Asp Tyr Ala Gly Leu Lys
1               5
<210> 2
<211> 9
<212> PRT
<213> Unknown
<220>
<223> synthetic peptide
<400> 2
Cys Lys Glu Asp Tyr Ala Gly Leu Lys
1               5
<210> 3
<211> 241
<212> PRT
<213> Homo sapiens
<400> 3
Met Ser Gly Glu Ser Ala Arg Ser Leu Gly Lys Gly Ser Ala Pro Pro
1               5                   10                  15
Gly Pro Val Pro Glu Gly Ser Ile Arg Ile Tyr Ser Met Arg Phe Cys
                20                  25                  30
Pro Phe Ala Glu Arg Thr Arg Leu Val Leu Lys Ala Lys Gly Ile Arg
            35                  40                  45
His Glu Val Ile Asn Ile Asn Leu Lys Asn Lys Pro Glu Trp Phe Phe
        50                  55                  60
Lys Lys Asn Pro Phe Gly Leu Val Pro Val Leu Glu Asn Ser Gln Gly
65                  70                  75                  80
Gln Leu Ile Tyr Glu Ser Ala Ile Thr Cys Glu Tyr Leu Asp Glu Ala
                85                  90                  95
Tyr Pro Gly Lys Lys Leu Leu Pro Asp Asp Pro Tyr Glu Lys Ala Cys
                100                 105                 110
Gln Lys Met Ile Leu Glu Leu Phe Ser Lys Val Pro Ser Leu Val Gly
            115                 120                 125
Ser Phe Ile Arg Ser Gln Asn Lys Glu Asp Tyr Ala Gly Leu Lys Glu
        130                 135                 140
Glu Phe Arg Lys Glu Phe Thr Lys Leu Glu Glu Val Leu Thr Asn Lys
145                 150                 155                 160
Lys Thr Thr Phe Phe Gly Gly Asn Ser Ile Ser Met Ile Asp Tyr Leu
                165                 170                 175
Ile Trp Pro Trp Phe Glu Arg Leu Glu Ala Met Lys Leu Asn Glu Cys
                180                 185                 190
Val Asp His Thr Pro Lys Leu Lys Leu Trp Met Ala Ala Met Lys Glu
            195                 200                 205
Asp Pro Thr Val Ser Ala Leu Leu Thr Ser Glu Lys Asp Trp Gln Gly
        210                 215                 220
Phe Leu Glu Leu Tyr Leu Gln Asn Ser Pro Glu Ala Cys Asp Tyr Gly
225                 230                 235                 240
Leu
<210> 4
<211> 241
<212> PRT
<213> Homo sapiens
<400> 4
Met Ser Gly Glu Ser Ala Arg Ser Leu Gly Lys Gly Ser Ala Pro Pro
1               5                   10                  15
Gly Pro Val Pro Glu Gly Ser Ile Arg Ile Tyr Ser Met Arg Phe Cys
                20                  25                  30
Pro Phe Ala Glu Arg Thr Arg Leu Val Leu Lys Ala Lys Gly Ile Arg
            35                  40                  45
His Glu Val Ile Asn Ile Asn Leu Lys Asn Lys Pro Glu Trp Phe Phe
        50                  55                  60
Lys Lys Asn Pro Phe Gly Leu Val Pro Val Leu Glu Asn Ser Gln Gly
65                  70                  75                  80
Gln Leu Ile Tyr Glu Ser Ala Ile Thr Cys Glu Tyr Leu Asp Glu Ala
                85                  90                  95
Tyr Pro Gly Lys Lys Leu Leu Pro Asp Asp Pro Tyr Glu Lys Ala Cys
                100                 105                 110
Gln Lys Met Ile Leu Glu Leu Phe Ser Lys Val Pro Ser Leu Val Gly
            115                 120                 125
Ser Phe Ile Arg Ser Gln Asn Lys Glu Asp Tyr Asp Gly Leu Lys Glu
        130                 135                 140
Glu Phe Arg Lys Glu Phe Thr Lys Leu Glu Glu Val Leu Thr Asn Lys
145                 150                 155                 160
Lys Thr Thr Phe Phe Gly Gly Asn Ser Ile Ser Met Ile Asp Tyr Leu
                165                 170                 175
Ile Trp Pro Trp Phe Glu Arg Leu Glu Ala Met Lys Leu Asn Glu Cys
                180                 185                 190
Val Asp His Thr Pro Lys Leu Lys Leu Trp Met Ala Ala Met Lys Glu
            195                 200                 205
Asp Pro Thr Val Ser Ala Leu Leu Thr Ser Glu Lys Asp Trp Gln Gly
        210                 215                 220
Phe Leu Glu Leu Tyr Leu Gln Asn Ser Pro Glu Ala Cys Asp Tyr Gly
225                 230                 235                 240
Leu

SEQUENCE LISTING

<160> NUMBER OF SEQ ID NOS: 6

<210> SEQ ID NO 1
<211> LENGTH: 8
<212> TYPE: PRT
<213> ORGANISM: Unknown
<220> FEATURE:
<223> OTHER INFORMATION: synthetic peptide

<400> SEQUENCE: 1

Lys Glu Asp Tyr Ala Gly Leu Lys
1               5

<210> SEQ ID NO 2
<211> LENGTH: 9
<212> TYPE: PRT
<213> ORGANISM: Unknown
<220> FEATURE:
<223> OTHER INFORMATION: synthetic peptide

<400> SEQUENCE: 2

Cys Lys Glu Asp Tyr Ala Gly Leu Lys
1               5

<210> SEQ ID NO 3
<211> LENGTH: 241
<212> TYPE: PRT
<213> ORGANISM: Homo sapiens

<400> SEQUENCE: 3

Met Ser Gly Glu Ser Ala Arg Ser Leu Gly Lys Gly Ser Ala Pro Pro
1               5                   10                  15

Gly Pro Val Pro Glu Gly Ser Ile Arg Ile Tyr Ser Met Arg Phe Cys
                20                  25                  30

Pro Phe Ala Glu Arg Thr Arg Leu Val Leu Lys Ala Lys Gly Ile Arg
            35                  40                  45

His Glu Val Ile Asn Ile Asn Leu Lys Asn Lys Pro Glu Trp Phe Phe
        50                  55                  60

Lys Lys Asn Pro Phe Gly Leu Val Pro Val Leu Glu Asn Ser Gln Gly
65                  70                  75                  80

Gln Leu Ile Tyr Glu Ser Ala Ile Thr Cys Glu Tyr Leu Asp Glu Ala
                85                  90                  95

Tyr Pro Gly Lys Lys Leu Leu Pro Asp Asp Pro Tyr Glu Lys Ala Cys
            100                 105                 110

Gln Lys Met Ile Leu Glu Leu Phe Ser Lys Val Pro Ser Leu Val Gly
        115                 120                 125

Ser Phe Ile Arg Ser Gln Asn Lys Glu Asp Tyr Ala Gly Leu Lys Glu
130                 135                 140

Glu Phe Arg Lys Glu Phe Thr Lys Leu Glu Glu Val Leu Thr Asn Lys
145                 150                 155                 160

Lys Thr Thr Phe Phe Gly Gly Asn Ser Ile Ser Met Ile Asp Tyr Leu
                165                 170                 175

Ile Trp Pro Trp Phe Glu Arg Leu Glu Ala Met Lys Leu Asn Glu Cys
            180                 185                 190

Val Asp His Thr Pro Lys Leu Lys Leu Trp Met Ala Ala Met Lys Glu
        195                 200                 205

Asp Pro Thr Val Ser Ala Leu Leu Thr Ser Glu Lys Asp Trp Gln Gly
210                 215                 220

```
Phe Leu Glu Leu Tyr Leu Gln Asn Ser Pro Glu Ala Cys Asp Tyr Gly
225                 230                 235                 240

Leu

<210> SEQ ID NO 4
<211> LENGTH: 241
<212> TYPE: PRT
<213> ORGANISM: Homo sapiens

<400> SEQUENCE: 4

Met Ser Gly Glu Ser Ala Arg Ser Leu Gly Lys Gly Ser Ala Pro Pro
1               5                   10                  15

Gly Pro Val Pro Glu Gly Ser Ile Arg Ile Tyr Ser Met Arg Phe Cys
            20                  25                  30

Pro Phe Ala Glu Arg Thr Arg Leu Val Leu Lys Ala Lys Gly Ile Arg
        35                  40                  45

His Glu Val Ile Asn Ile Asn Leu Lys Asn Lys Pro Glu Trp Phe Phe
50                  55                  60

Lys Lys Asn Pro Phe Gly Leu Val Pro Val Leu Glu Asn Ser Gln Gly
65                  70                  75                  80

Gln Leu Ile Tyr Glu Ser Ala Ile Thr Cys Tyr Leu Asp Glu Ala
                85                  90                  95

Tyr Pro Gly Lys Lys Leu Leu Pro Asp Asp Pro Tyr Lys Ala Cys
            100                 105                 110

Gln Lys Met Ile Leu Glu Leu Phe Ser Lys Val Pro Ser Leu Val Gly
        115                 120                 125

Ser Phe Ile Arg Ser Gln Asn Lys Glu Asp Tyr Asp Gly Leu Lys Glu
130                 135                 140

Glu Phe Arg Lys Glu Phe Thr Lys Leu Glu Glu Val Leu Thr Asn Lys
145                 150                 155                 160

Lys Thr Thr Phe Phe Gly Gly Asn Ser Ile Ser Met Ile Asp Tyr Leu
                165                 170                 175

Ile Trp Pro Trp Phe Glu Arg Leu Glu Ala Met Lys Leu Asn Glu Cys
            180                 185                 190

Val Asp His Thr Pro Lys Leu Lys Leu Trp Met Ala Ala Met Lys Glu
        195                 200                 205

Asp Pro Thr Val Ser Ala Leu Leu Thr Ser Glu Lys Asp Trp Gln Gly
210                 215                 220

Phe Leu Glu Leu Tyr Leu Gln Asn Ser Pro Glu Ala Cys Asp Tyr Gly
225                 230                 235                 240

Leu

<210> SEQ ID NO 5
<211> LENGTH: 9
<212> TYPE: PRT
<213> ORGANISM: Unknown
<220> FEATURE:
<223> OTHER INFORMATION: synthetic peptide

<400> SEQUENCE: 5

Cys Lys Glu Asp Tyr Asp Gly Leu Lys
1               5

<210> SEQ ID NO 6
<211> LENGTH: 9
<212> TYPE: PRT
<213> ORGANISM: Unknown
<220> FEATURE:
<223> OTHER INFORMATION: synthetic peptide
```

```
<400> SEQUENCE: 6

Lys Glu Asp Tyr Ala Gly Leu Lys Cys
1               5
```

We claim:

1. A polypeptide hapten having a structure selected from the group consisting of (SEQ ID NO: 2)
Cys-Lys-Glu-Asp-Tyr-Ala-Gly-Leu-Lys; and (SEQ ID NO 6)
Lys-Glu-Asp-Tyr-Ala-Gly-Leu-Lys-Cys;

wherein a crosslinking group is attached to the sulphur atom of Cys.

2. An immunogen comprising the polypeptide hapten of claim 1 coupled to an immunogenicity conferring carrier molecule.

3. An isolated antibody raisable from the immunogen of claim 2 which specifically binds to wtGSTO1 (SEQ ID NO: 3)and does not bind to mutGSTO1 (SEQ ID NO: 4).

4. The isolated antibody of claim 3 which is a monoclonal antibody.

5. A method for the detection and/or determination of wtGSTO1 in an in vitro patient sample, the method comprising:

contacting the patient sample with an antibody of claim 4 and means to detect binding by said antibody with a detecting agent, detecting and/or determining any signal produced by the detecting agent means by reference to one or more calibrators, in which the presence of a detectable or quantifiable signal indicates the presence or amount of wtGSTO1.

6. A kit for detecting and/or determining the presence of wtGSTO1 (SEQ ID NO: 3), in a sample, the kit comprising the antibody of claim 3 and means to detect binding by said antibody.

7. The kit of claim 6, wherein the antibody is a monoclonal antibody.

8. The kit of claim 6, further comprising a detecting agent that recognizes a common epitope of wtGSTO1 (SEQ ID NO: 3) and mutGSTO1 (SEQ ID NO: 4).

9. The kit of claim 7, comprising a detecting agent that recognizes a common epitope of wtGSTO1 (SEQ ID NO: 3) and mutGSTO1 (SEQ ID NO: 4).

10. The kit of claim 8, further comprising an antibody which binds both wtGSTO1 (SEQ ID NO: 3) and mutGSTO1 (SEQ ID NO: 4); and the kit additionally comprises one or more detecting agents.

11. The kit of claim 7, further comprising an antibody which binds both wtGSTO1 (SEQ ID NO: 3) and mutGSTO1 (SEQ ID NO: 4); and the kit additionally comprises one or more detecting agents.

12. The antibody of claim 3 wherein the isolated antibody has a cross-reactivity of less than 0.1% for mutGSTOl (SEQ ID NO: 4), when compared with wtGSTO1 (SEQ ID NO: 3).

13. The antibody of claim 4 wherein the isolated antibody has a cross-reactivity of less than 0.1% for mutGSTO1 (SEQ ID NO: 4), when compared with wtGSTO1 (SEQ ID NO: 3).

14. The kit of claim 6 wherein the isolated antibody has a cross-reactivity of less than 0.1% for mutGSTO1 (SEQ ID NO: 4), when compared with wtGSTO1 (SEQ ID NO: 3).

15. The kit of claim 7 wherein the isolated antibody has a cross-reactivity of less than 0.1% for mutGSTO1 (SEQ ID NO: 4), when compared with wtGSTO1 (SEQ ID NO: 3).

\* \* \* \* \*